United States Patent [19]
Clawson et al.

[11] Patent Number: 5,455,005
[45] Date of Patent: Oct. 3, 1995

[54] MATERIAL REMEDIATION IN MULTI-FUNCTION HEATING DRUM

[75] Inventors: Lawrence G. Clawson, Dover, Mass.; Joseph E. Musil, Ely, Iowa

[73] Assignee: Cedarapids, Inc., Cedar Rapids, Iowa

[21] Appl. No.: 318,375

[22] Filed: Oct. 5, 1994

Related U.S. Application Data

[62] Division of Ser. No. 135,917, Oct. 13, 1993, Pat. No. 5,393,501.

[51] Int. Cl.$^6$ ........................................ A61L 2/06
[52] U.S. Cl. ........................ 422/1; 422/32; 432/105; 432/111; 432/112; 34/135; 34/136; 34/137; 110/226; 110/236; 110/246; 588/208; 588/228
[58] Field of Search ................ 422/32.1; 588/900, 588/209, 213, 220, 228–230, 234, 240, 245; 110/240, 236, 226, 246; 432/104, 107; 431/5, 9, 115, 116; 34/108, 130, 132, 606, 135–137; 366/24–25; 198/733, 731, 546–547

[56] References Cited

U.S. PATENT DOCUMENTS

| | | | |
|---|---|---|---|
| Re. 29,496 | 12/1977 | Dydzyk | 366/25 |
| 3,054,193 | 9/1962 | Wright | 34/137 |
| 3,219,173 | 11/1965 | Baker | 198/733 |
| 3,652,194 | 3/1972 | Bailey | 431/9 |
| 4,011,023 | 3/1977 | Cutler | 404/91 |
| 4,205,458 | 6/1980 | Austin | 34/135 |
| 4,298,337 | 11/1981 | Butler et al. | 431/285 |
| 4,427,293 | 5/1984 | Campbell | 405/126 |
| 4,427,376 | 1/1984 | Etnyre et al. | 432/105 |
| 4,493,309 | 1/1985 | Wedge et al. | 431/116 |
| 4,522,498 | 6/1985 | Mendenhall | 366/25 |
| 4,600,377 | 7/1986 | Musil | 431/351 |
| 4,600,379 | 7/1986 | Elliott | 432/13 |
| 4,667,609 | 5/1987 | Hardison et al. | 110/236 |
| 4,705,404 | 11/1987 | Brüggemann | 366/7 |
| 4,730,564 | 3/1988 | Abboud | 110/246 |
| 4,787,938 | 11/1988 | Hawkins | 432/14 |
| 4,870,911 | 10/1989 | Chang et al. | 110/246 |
| 4,925,389 | 5/1990 | Decicco et al. | 432/106 |
| 4,957,429 | 9/1990 | Mendenhall | 432/105 |

(List continued on next page.)

FOREIGN PATENT DOCUMENTS

| | | | |
|---|---|---|---|
| 5020237 | 1/1992 | Germany | 431/116 |
| 563820 | 6/1957 | Italy | 431/116 |
| 54-11531 | 1/1979 | Japan | 431/115 |

*Primary Examiner*—Robert J. Warden
*Assistant Examiner*—Hien Tran
*Attorney, Agent, or Firm*—Simmons, Perrine, Albright & Ellwood

[57] ABSTRACT

Material remediation apparatus includes a remediation drum through which materials, such as soil contaminated with hydrocarbons, are advanced from a feed end to a discharge end of the drum. A tube extending concentrically from the discharge end of the drum into the drum forms a combustion chamber. Materials being decontaminated advance through an annular space between the tube and the drum. The tube is axially first of converging and then of diverging shape, as viewed from the discharge end of the drum. A turbo burner injects combustible gases into the tube which are burned within the diverging shape of the tube. A portion of the burned gases reflow from the outlet of tube through the annular space to the discharge end of the drum. In a zone of the drum occupied by the tube materials are heated by conduction and radiation of energy passing through the wall of the tube as well as by convective heating from the reflow gases. Hot gases are exhausted from the drum at the feed end thereof. However, hydrocarbons volatilized by the heating process in the annular space first pass with the reflow gases through the combustion chamber and are burned before being exhausted. The exhaust gases are filtered in a baghouse filter. Materials from which hydrocarbons have been extracted by volatilization in the annular space are cooled and reconstituted by water injection. Steam generated as a result of the water injection is filtered in a separate filter section of the baghouse filter.

10 Claims, 4 Drawing Sheets

U.S. PATENT DOCUMENTS

| | | | |
|---|---|---|---|
| 4,995,807 | 2/1991 | Rampley et al. | 431/9 |
| 5,067,254 | 11/1991 | Linketter et al. | 34/135 |
| 5,088,856 | 2/1992 | Yocum | 110/346 |
| 5,164,158 | 11/1992 | Brashears et al. | 422/1 |
| 5,192,204 | 3/1993 | Musil | 431/10 |
| 5,252,124 | 10/1993 | Brashears et al. | 588/209 |
| 5,275,554 | 1/1994 | Faulkner et al. | 431/115 |

MATERIAL REMEDIATION IN MULTI-FUNCTION HEATING DRUM

This is a divisional application of parent application Ser. No. 08/135,917, filed Oct. 13, 1993, entitled "MATERIAL REMEDIATION IN MULTI-FUNCTION HEATING DRUM", which issued Feb. 28, 1995, as U.S. Pat. No. 5,393,501.

BACKGROUND OF THE INVENTION

The invention relates generally to methods of and apparatus for solid material remediation, using heat energy for the volatilization, disassociation and detoxification of contaminants. More particularly, the invention relates to methods of and apparatus for solid material remediation, using hot gases to adsorb and drive contaminants from the solid materials, and then to subject the hot gases including the contaminants to further heating to break down and detoxify the contaminants, such as by oxidation. These processes and related apparatus have been used to decontaminate soil which has become contaminated by, for example, oil or gasoline spills.

Various types of apparatus and methods are known, all of which perform a similar function, namely to first volatilize contaminants and then heat the contaminants to break down the molecular structure and to oxidize the contaminants before the exhaust is emitted into the atmosphere. Thus, in general, a decontamination procedure includes two steps. First, the contaminants, in most instances hydrocarbons, are volatilized and thereby removed from the solid materials. In a second series of steps, the volatilized contaminants need to either be removed from the gaseous carrier medium or they need to be chemically altered into environmentally acceptable compounds. Some contaminants may require scrubbers, which are known and available. Generally, though, in the case of the contaminants being hydrocarbons, the volatilized contaminants are burned in a high temperature process to form non-objectionable carbon dioxide and water vapor.

Much effort has already gone into improving this general process to bring down the cost of remediation of solid material contaminated with hydrocarbons. It appears that more effort in development and further improvements are needed in the technological field of soil remediation. As long as gasoline and fuel oils remain a major source of energy for our society, oil spills tend to remain a constant threat to the environment. Since soil typically has a certain moisture content, removal of hydrocarbons by heat becomes more complicated by a concurrent vaporization of water and associated cooling of the material to be decontaminated. Also, hydrocarbon contamination may contain a mixture of lighter, short-chain and heavier, long-chain hydrocarbons. The lighter hydrocarbons may volatilize at a temperature at or below that at which water contained in the material to be decontaminated forms steam. Thus, lighter hydrocarbons may be removed with water vapor and may need to be separated from the water vapor. Heavier, long-chain hydrocarbon fractions are not so readily volatilized and need to be separated from the soil material at temperatures well above those at which water is boiled off from the soil. Two steps of soil decontamination have in the past required apparatus which is complex and comparatively costly to transport, set up and maintain. Improvement in efficiency of cleaning up oil spills may be brought about by improvements in any of a number of ways. Cost reduction may result from a simplification of known decontamination apparatus. The cost of transporting apparatus to a site may be improved by making the remediation equipment more compact. The efficiency of removing hydrocarbons from bulk material may further become improved by an increase in throughput capacity of a soil remediation apparatus, or by a decrease in an energy requirement to process a given amount of contaminated material.

SUMMARY OF THE INVENTION

It is therefore an object of the invention to improve known methods of and apparatus for remediating solid materials, such as soil, by generally improving the efficiencies of a process of removal of contaminants from the solid materials and by providing a single drum remediation apparatus which features multiple soil remediation functions.

It is another object of the invention to provide compact apparatus for removing contaminants from solid materials.

It is another object of the invention to provide apparatus having a single burner unit, which apparatus functions to drive off contaminants through a combination of conductive, convective and radiant heat transfer.

A further object of the invention is to provide a material reconstitution apparatus with provisions for heating exhaust gases to a temperature sufficiently above water vapor condensation temperatures to keep the water vapor from condensing in a subsequent filtering operation.

Yet another object of the invention is to provide a dust separator unit with multiple, separate dust separation chambers.

According to the invention a solid material remediation system comprises a remediation drum which is mounted for rotation about a longitudinal axis which is inclined with respect to the horizontal. The remediation drum has a burner unit disposed at a material discharge end of the drum. The remediation drum has a material intake chamber at a first, material intake end of the drum and a material discharge chamber at a second, material discharge end opposite from the material intake end. The burner unit is preferably a turbo burner unit, which is disposed at the material discharge end of the drum and which is disposed to direct a combustible mixture of air and fuel into the drum to flow in a counterflow direction with respect to the material from the material discharge end toward the material intake end of the drum. The remediation drum is divided into first and second heating zones. The first heating zone extends from adjacent to the material intake end inwardly to a zone boundary intermediate the material intake and material discharge ends of the remediation drum. The second heating zone extends from the zone boundary toward and essentially to the material discharge end of the remediation drum. A combustion chamber is disposed within and extends the length of the second heating zone of the remediation drum from the zone boundary to substantially the material discharge end of the remediation drum. The combustion chamber includes a combustion chamber tube which is concentrically disposed within the remediation drum. The combustion chamber tube has a gas-entraining converging inlet opening adjacent to the material discharge end of the remediation drum and then an outwardly flared flameholder section, followed by an outlet section adjacent to the zone boundary leading to the first heating zone.

Of particular advantage to the operation of the drum in accordance herewith is a mounting of the combustion chamber tube concentrically with respect to the drum. An annular gap between an outer surface of a wall of the combustion chamber tube and an inner surface of a cylindrical wall of the drum constitutes a passage for solid materials being conveyed toward the discharge end of the drum and a gaseous return flow of hot combustion gases from the first heating zone to an inlet to the combustion chamber tube adjacent to the discharge end of the remediation drum.

A particular structure within the scope of the invention and advantageous to furthering the objects thereof has the combustion chamber tube concentrically and co-rotationally mounted with respect to the drum.

According to a modification, the combustion chamber tube may be comprised of a split combustion chamber tube in which a gas entraining converging section and a parallel flow or orifice section is fixedly mounted and a diverging flame section of the combustion chamber tube is mounted to the drum to co-rotate with the drum and rotate with respect to the fixed converging and orifice sections of the combustion chamber tube.

According to yet another variation, the combustion chamber tube may be, in its entire length, cantilevered from a supporting structure at a discharge end of the drum to extend in a non-rotating manner into the interior space of the drum. The foregoing alternative structures may be used to allow a flame holder and pilot flame assembly to extend, supported by the combustion chamber tube, into the combustion chamber tube, toward the diverging section of the combustion chamber tube which serves as the flame region or section thereof.

A material reconstitution chamber, which may be separate from the remediation drum, preferably has an elongate base housing of rectangular cross section, an endless paddle chain conveyor mounted therein for advancement of the material, and a steam dome extending above the base housing. The material reconstitution chamber receives heated and remediated material from the remediation drum, and the paddle chain advances and mixes the heated material while water is being added to cool and reconstitute the material. Steam which is generated as a result of water contacting the heated material is drawn off and routed to a dust separator.

A dust separator unit in accordance herewith has first and second filter houses mounted on a common frame, and a dust collection chamber and ejector of the first filter house may open into the dust collection chamber of the second filter house. A single common dust ejector discharges dust which may be added to the solid material at the material reconstitution chamber.

Other features and advantages of the invention will become apparent from the Detailed Description below.

BRIEF DESCRIPTION OF THE DRAWINGS

The Detailed Description including the description of a preferred structure as embodying features of the invention will be best understood when read in reference to the accompanying figures of drawing wherein.

DETAILED DESCRIPTION OF THE INVENTION

1. A System Overview

Figure 1:
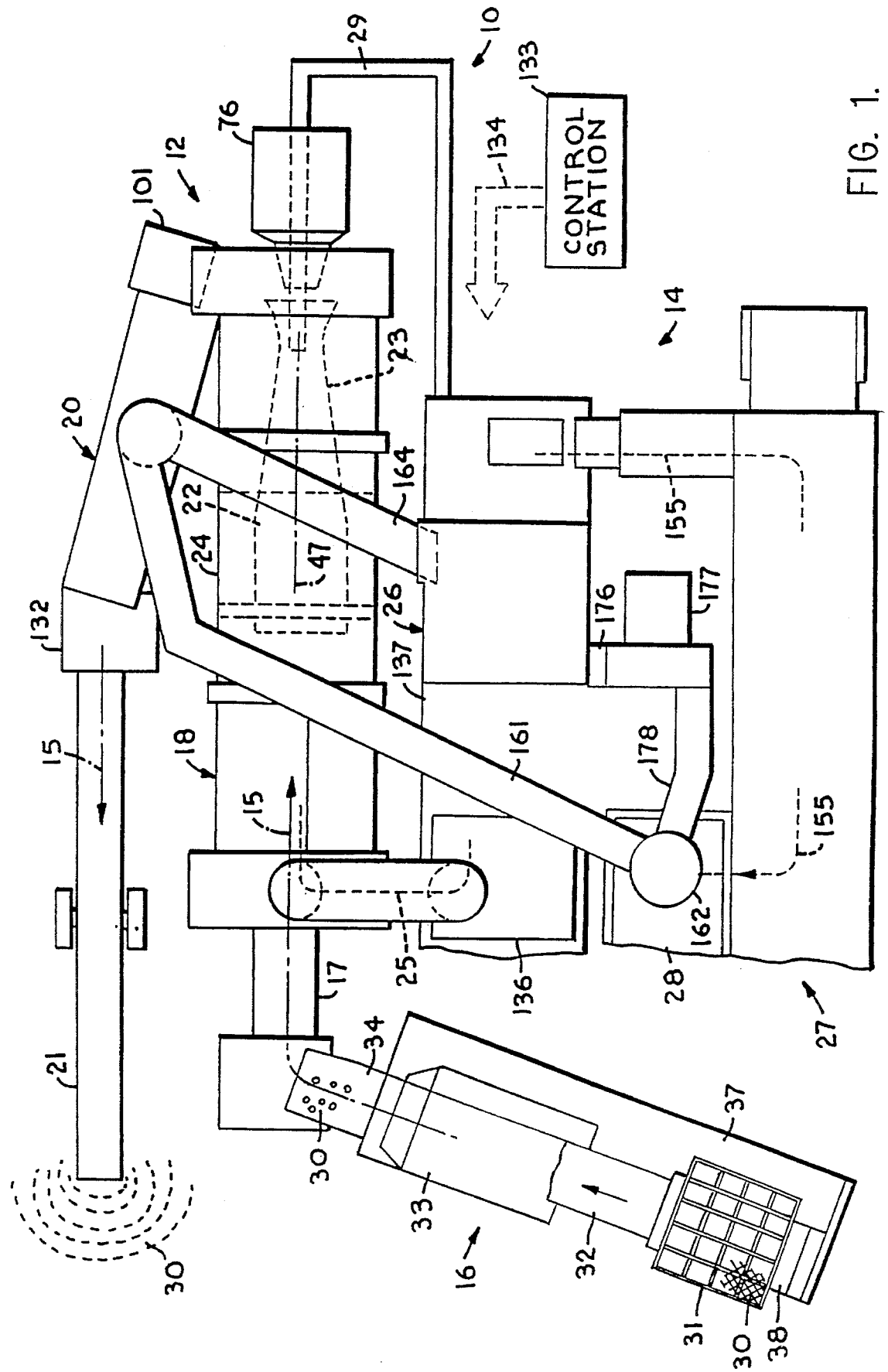
FIG. 1 is a schematically simplified plan view of a solid material remediation system giving an overview of features related to the subject matter of the invention and their relationship to the remediation system in accordance herewith.

FIG. 1 shows, somewhat simplified, a plan view of a solid material remediation system, which is designated generally by the numeral 10. The material remediation system 10 includes a solid material decontamination subsystem 12 and an emission cleaning subsystem 14. The solid material decontamination subsystem 12 includes system elements in a solid material process path 15 including, as a preferred example, a soil preparation and feeder unit 16, a feeder conveyor 17, a solid material remediation drum unit 18, a soil reconstitution unit 20, and a product delivery conveyor 21. The emission cleaning subsystem 14 includes the solid material remediation drum unit 18, which, in addition to being the solid material remediation apparatus, also functions as a first stage of an emission cleaning apparatus. As will be appreciated, the solid material decontamination subsystem 12 and the emission cleaning subsystem 14 cooperatively interact in, and share, the material remediation drum unit 18 for respective decontamination and exhaust cleaning functions.

Particularly, a combustion chamber 22 is the interior space of a combustion chamber tube 23. The combustion chamber tube 23 is disposed in concentric relationship to a drum 24 of the remediation drum unit 18. The cooperative relationship of the combustion chamber tube 23 and the drum 24 forms a first cleaning stage of hot gases in a path 25 of hot gases through the emission cleaning subsystem 14. From the drum unit 18, the hot gases 25 advance to a dust removal unit, which may be, as a preferred example, a combination cyclone-and-baghouse filter unit 26 and an afterburner unit 27. Gases from the afterburner unit 27 are emitted to the atmosphere through an exhaust stack unit 28.

The solid material remediation system 10 as described herein is particularly adapted for the removal of hydrocarbon type contaminants from soil. It is understood that other contaminants, such as sulphur or chlorine containing compounds, may require added scrubber units or catalytic combustor units (not shown) to be interposed into the path of apparatus for cleaning the exhaust gases before they are emitted through the exhaust stack unit 28 into the atmosphere.

Referred-to apparatus of the solid material decontamination subsystem 12 and of the emission cleaning subsystem 14 interact at points other than in the remediation drum unit 18 in an advantageous manner. Thus, the soil reconstitution unit 20 generates a substantial amount of steam as a result of water being introduced into the reconstitution unit 20 to cool and reconstitute the hot and dry material fed to the unit 20. The generated steam contains dust or fines but is essentially free of hydrocarbon contaminants. The generated steam, consequently, is routed for dust removal to the filter unit 26 before being vented through the exhaust stack unit 28 to the atmosphere. The steam generated by the soil reconstitution unit 20 is a wet steam, essentially at a temperature of 200 degrees F. (Fahrenheit). Since the wet steam and dust combination would tend to form a clogging sludge in a baghouse filter, the temperature of the steam or off-gas from the reconstitution unit 20 is preferably raised to permit it to be filtered before being released to the atmosphere. The wet steam is consequently conveniently mixed with filtered exhaust gases from the afterburner unit 27 before they are released through the exhaust stack unit 28. The hot exhaust gases are controllably mixed with the steam generated at the soil reconstitution unit 20 to raise the temperature of the mixture of the steam and exhaust gas mixture into a range of about four hundred degrees F., well above the condensation temperature of water. Dust collected at the filter unit 26 may be transferred to and re-introduced into the drum 24, such as by a typical screw or auger conveyor depicted schematically by dust return line 29. Alternatively, the dust might be combined with the decontaminated soil in the soil reconstitution unit 20. The manner of handling the dust is, however, a matter of choice within the scope of the invention.

2. The Solid Material Decontamination Subsystem

Further in reference to FIG. 1, material 30 enters the solid material decontamination subsystem 12 upon being delivered to a material feed hopper 31 of the soil preparation and feeder unit 16. The soil preparation and feeder unit 16 is preferred to be a single, "closed circuit" unit, as shown. Soil preparation and feeding functions, however, may be accomplished by separate units mounted in cooperative relationship to each other. The preferred soil preparation and feeder unit 16 includes a typical feeder structure 32, which is disposed at a base of the feed hopper 31 and which meters and feeds solid materials at a relatively stable rate from the feed hopper 31 to a vibrating screen 33. Selected mesh sizes of the vibrating screen 33 pass ideally-sized soil 30 (solid material) to a conveyor 34 which, in turn, transfers the soil 30 to the feeder conveyor 17 leading into the remediation drum unit 18. The feeder conveyor 17 may be any one of a known type of feeder conveyors, preferably a belt conveyor including a material measuring device, which is known in the art as a weigh bridge. Weigh bridges are used in conjunction with belt conveyors, such as the conveyor 17. Knowing an instantaneous amount of material on the conveyor, by weight, and the speed of the conveyor 17 permits one to calculate the material mass flow rate in a well known manner. Oversize material, which fails to pass through mesh openings of screens on the vibrating screen unit 33, is routed by a conveyor 37 to a comminution apparatus, such as a small crusher 38, before being returned for another feed cycle through the vibrating screen 33. Oil contaminated soil 30 is found to have a tendency of caking and yielding relatively large lumps of soil. A relatively large chunk of soil may not become fully penetrated by heat energy during the heating process within the remediation drum unit 18. Hydrocarbons may not become fully volatilized during that time. Breaking the contaminated soil lumps into relatively small chunks of material facilitates heat penetration and volatilization of the hydrocarbons in the soil 30. Thus, the soil preparation and feeder unit 16 prepares the soil for remediation in a complete sizing cycle which causes only that material to be fed to the remediation drum unit 18 which is correctly sized to become fully treated during the time it takes the soil 30 to advance through the remediation drum unit 18.

Figure 2:
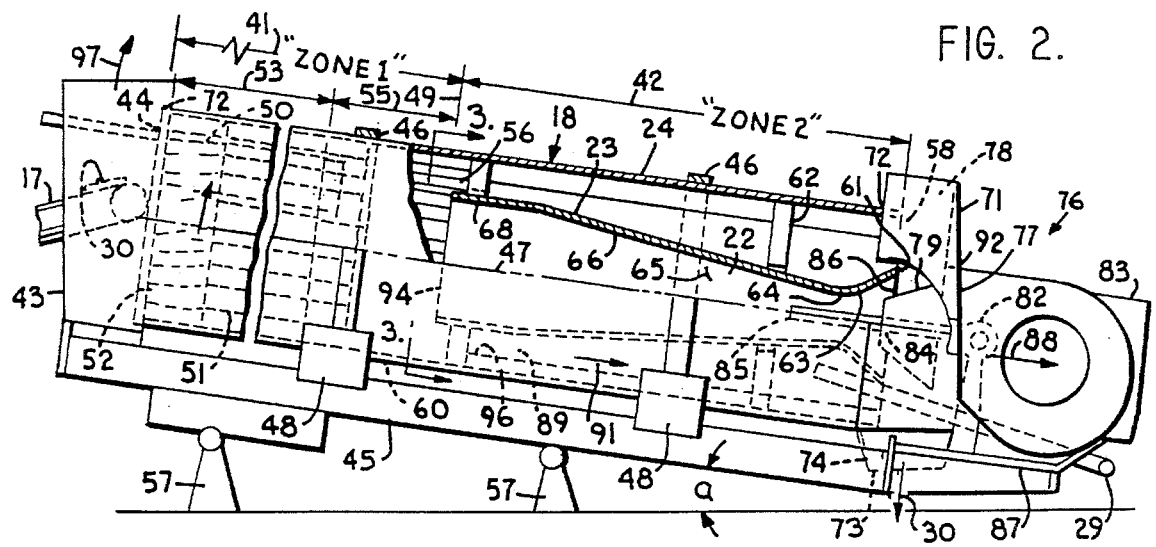
FIG. 2 is a cut away view of a remediation drum in FIG. 1.
Figure 3:
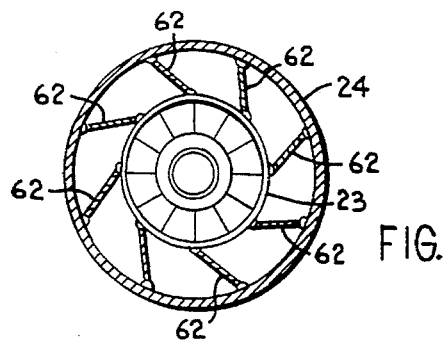
FIG. 3 is a cross-sectional view through the remediation drum showing mounting details of a combustion chamber within the remediation drum.

Advantages of the remediation drum unit 18 are best seen in reference to FIGS. 2 and 3. The remediation drum unit 18 is functionally divided into first and second heating zones 41 and 42, respectively, as a preferred example of a multi-function material heating apparatus 18. In the preferred dual-zone material heating apparatus 18, the first heating zone 41 (which is shown somewhat foreshortened) is the heating zone to which the solid material or soil 30 is delivered by the feeder conveyor 17. The feeder conveyor 17 extends through a stationary feed intake housing 43 at a material intake end 44 of the drum 24. The feed intake housing 43 may be mounted to and supported by a truck frame or support frame 45 of the remediation drum unit 18. The drum 24 of the remediation drum unit 18 is rotatably supported with respect to the support frame 45 in a convenient manner, such as by tires 46. The drum 24 is driven to rotate about a longitudinal axis 47 in a convenient manner, such as by a chain drive or by powered trunnion assemblies 48 to engage and drive the tires 46.

The first heating zone 41 extends from the material intake end 44 of the drum 24 axially inward to a boundary 49 with the second heating zone 42. The first heating zone 41 advances the material with intake flights 50 into the drum 24. The intake flights 50 are generally skewed or spirally oriented within the drum 24 to advance the material 30 from the intake end 44 into the drum 24. The intake flights 50 are then followed by veiling flights or material lift flights 51 mounted to an inner cylindrical surface 52 and extending over a major heating section 53 of the first heating zone 41. A function of the lift flights 51 or bucket flights is well known in the art. As the drum 24 rotates about its longitudinal axis 47, the bucket flights 51, when in a lower quarter of rotation of the drum 24, fill up with the material 30 and begin to lift the material 30 peripherally as the drum 24 rotates. As the flights 51 pass a plane of a transverse horizontal axis and the longitudinal axis 47, the material 30 slowly begins to "spill" from the flights 51 and cascades back to the base of the drum 24, as the drum 24 continues to rotate. Thus, a curtain or veil of the material 30 cascades from the periphery through an interior, cylindrical space of the drum 24. The described operation of the lift flights 51 of continuously and repeatedly lifting and then dropping the material 30 in a veil is commonly used in drum driers. Hot gases are routed through the space of drum driers, and the veil of material falls through the hot gases. The use of the veiling or lift flights 51 is considered well known in aggregate driers for asphalt material preparation, as well as in soil remediation apparatus using drier drums. A baffle plate assembly (not shown), known as a veil modification kit 5, which is fully disclosed in U.S. Pat. No. 5,067,254, may be used within the drum 24 to control heat transfer from the hot gas stream to the material 30.

A transition section 55 of the first heating zone 41 preferably features combustor or heat shield flights 56 in lieu of the bucket flights 51. As can be ascertained from FIG. 2, the remediation drum unit 18 is preferably mounted with its longitudinal axis 47 disposed at an inclined angle "a" with respect to the horizontal. The support frame 45 may be supported with respect to the ground by footings or by jacks 57 at any of various different angles with respect to ground or a horizontal, to establish a desired angle "a" of a preferred inclination of the drum 24. The angle "a" of inclination is known to affect the rate of flow of the material 30 through the drum 24. Though the drum 24 may be regarded as being disposed generally horizontally, as opposed to being steeply inclined in an almost vertical orientation, the angle "a" of inclination of the drum 24 from a horizontal plane is chosen to cause the material within the drum 24 to slowly advance from the intake end 44 toward a discharge end 58 of the drum 24. Each time the material 30 is lifted by the bucket flights 51 and drops in the veil of material 30, the material advances toward the discharge end 58. Within the transition section 55, the combustor flights 56 are disposed to replace the function of lifting and dropping the material 30 in a veil of the bucket flights 51. Instead, the material 30 is maintained preferably in a peripheral region relative to the gases exiting from the combustion chamber tube 23. The combustor flights 56 are disposed generally parallel to the longitudinal axis 47 or the drum 24. Any direction of slant of any of the flights, such as the intake flights 50, would, however, cooperate with a design direction of rotation of the drum 24, as indicated by arrow 59, to push or advance the material 30 toward the discharge end 58 of the drum 24. Thus, a forward material movement toward the discharge end 58 continues, even though the materials 30 tend to remain substantially in a peripheral region 60 of the drum 24.

The second heating zone 42 is considered to coincide with a length of the drum 24 through which the combustion chamber tube 23 extends. The combustion chamber tube 23 has a gas intake end 61 disposed substantially even with the discharge end 58 of the drum 24 and is centrally or concentrically supported within the drum 24 by a plurality of peripherally spaced support links 62. From the discharge end 58, the combustion chamber tube 23 extends into the drum 24, essentially centered on the longitudinal axis 47. The support links 62 extend in a plane transverse to the longitudinal axis 47 of the drum 24 and are disposed at an angle of inclination with respect to a true radial direction in a transverse plane corresponding to a sectional plane through the drum 24 as depicted in FIG. 3. The support links 62 are pivotally attached to the inner wall of the drum 24 and to the outer wall of the combustion chamber tube 23, the pivotal movement being restricted to a plane transverse to the longitudinal axis 47 relative to the combustion chamber tube 23 and the drum 24. Thus, the position of the combustion chamber tube 23 in its longitudinal direction remains centered with respect to the drum 24. In a thermal expansion and contraction cycle of the combustion chamber tube 23 during the operation of the remediation drum unit 18, the support links 62 function as thermal expansion links 62. The thermal expansion links 62 provide for a substantially stress free differential thermal expansion of the combustion chamber tube 23 relative to the drum 24. The concentric position of the combustion chamber tube 23 relative to the drum 24 remains intact in spite of a thermal expansion of the combustion chamber tube 23 diameter which may differ from a thermal expansion of the diameter of the drum 24. The links 62 translate any differential expansion between the combustion chamber tube 23 and the drum 24 into angular displacement of one with respect to the other.

The combustion chamber tube 23 is of compound shape along its length coextensive of the longitudinal axis 47. From the discharge end 58 of the drum 24, the combustion chamber tube 23 extends inward from the gas intake end 61 along the length of the drum 24 with a first, bell-shaped, interiorly convex, converging gas intake section 63. The gas intake section 63 or gas entraining section 63 transitions through a parallel flow nozzle section or orifice section 64 into a diverging flame region 65 having a conically diverging wall section 66, all converging or diverging sections of the combustion chamber tube 23 being considered as having their respective shapes in the direction of gaseous flow therethrough. The diverging flame region 65 of the combustion chamber tube 23 transitions again into a forward combustion chamber extension 67 having a preferably cylindrical wall section 68 extending parallel to the drum 24. A length of the cylindrical wall section 68 may be chosen to vary the degree of combustion occurring within the combustion chamber tube 23. However, the cylindrical section 68 may be modified or even omitted, depending on the gas flow within the combustion chamber tube 23 and on an amount of reflow of combustion gases which may be desired in accordance herewith. Also, a radial flow component of gases leaving the combustion chamber tube 23 may be generated by a final trumpet shaped exit end (not shown) to decrease the flow velocity of the gases entering the first heating zone 41 and aid a return flow of gases externally of the combustion chamber tube 23.

A stationary discharge housing 71 caps off the discharge end of the drum 24. Both the discharge housing 71 and the feed intake housing 43 are sealed against the rotatable drum 24 by respective peripheral seals 72, also referred to herein as discharge chute 73. A material discharge chute 73 as a lower extension of the discharge housing 71, would include a material actuated discharge gate 74. The discharge gate 74 allows the material 30 to exit, but seals the discharge chute 73 from air being admitted into the discharge housing 71. Thus, the discharge gate 74 would remain closed in the absence of material in the chute 73 to prevent ambient air from being drawn into the discharge housing 71.

A burner assembly 76, preferably a turbo burner assembly 76, is mounted to one end of the support frame 45 adjacent to the remediation drum unit 18. The burner assembly 76 extends through an opening 77 in the discharge housing 71 through a discharge chamber 78 formed by the discharge housing 71. A possible matching gap or space between the burner assembly 76 and the discharge housing 71 is also sealed, in conformance with an intended operation of the burner assembly 76, to restrict ambient air from entering into the discharge housing 71. Thus, the interior of the discharge housing 71 is substantially sealed off from receiving any amounts of ambient air to an extend that will affect the intended operation of a gas reflow process as described herein. A burner head or converging burner nozzle 79 extends into the converging intake section 63 of the combustion chamber tube 23. The burner assembly 76 is shown as a complete assembly for supplying turbo blower combustion air and for injecting into the air a fuel spray to mix with the combustion air in a known manner. The burner assembly 76 is considered to include a fuel injector assembly 82 coupled to a fuel supply schematically shown at 83. The burner assembly 76 would include an ignitor assembly or pilot flame assembly 84 having a flame holder 85 at its outer end. The flame holder 85 is preferably located within the interior of the combustion chamber tube 23, i.e., past the orifice section 64 and into the diverging flame region 65. It has been found that the converging-diverging gaseous flow characteristics of the combustion chamber tube 23 tend to inhibit a flame from passing through the throat or orifice section 64 of the combustion chamber tube 23. Thus, a preferred embodiment contemplates a coaxial routing of the pilot flame assembly 84 directly through the burner nozzle 79 and past the orifice section 64 into the diverging flame section 65 of the combustion chamber tube 23. Other structures may be used to extend the pilot flame assembly 84 past the orifice section 64 of the combustion chamber tube 23, for example, routing its elongated tube between the converging intake end or gas intake end 61 of the combustion chamber tube 23 and the burner nozzle 79. Functionally the burner assembly 76 mixes turbo-blower air with fuel and is contemplated to inject, in accordance herewith, a high velocity stream of combustible gases, made up of the air and fuel mixture through the burner nozzle 79, into the combustion chamber tube 23. A rate at which the burner assembly 76 injects the combustible gases into the combustion chamber tube 23 may vary depending on the desired quantity of heat energy needed in the operation of the remediation drum unit 18. The velocity of the stream of combustible gases upon entering the combustion chamber tube 23 lies in a range which generally exceeds the flame speed of combustion, such that the flame does not blow back to the gas intake end or gas entry end 61 of the combustion chamber tube 23. The velocity of the gas stream in such range is designated herein as being high. A pressure-velocity head of the gas stream is substantially a velocity head at the high gas velocity. The gases entering the combustion chamber tube 23 generate a comparatively low pressure area, with respect to the static gas pressure, about the gas intake end 61 of the combustion chamber tube 23. According to a preferred embodiment, as may have become apparent, the combustible gases injected by the burner assembly 76 are not ignited until after they have been injected into the combustion chamber tube 23. The pilot flame assembly 84 will ignite the injected gases and sustain a flame within the combustion chamber tube 23 during start up conditions or when the rate of injection of the combustible gases from the burner assembly 76 is turned down to or below a minimum setting.

The converging burner nozzle 79 is, in accordance herewith, adjustable along the longitudinal axis 47 through the drum 24 with respect to the gas intake section 63 of the combustion chamber tube 23. A longitudinal adjustment of the converging burner nozzle 79 with respect to the gas intake section 63 of the combustion chamber tube 23 is employed to widen or narrow a gap 86 between the combustion chamber tube 23 and the burner nozzle 79. A desired adjustment is contemplated to be advantageously accomplished by either a slidable adjustment of a burner base 87 either toward or away from the drum 24 along the frame 45, as indicated by arrow 88, or, preferably, by the burner nozzle 79 being extendable with respect to the remainder of the burner assembly 76.

Adjustment of the width of the gap 86 controls the amount of combustion gases which are caused to reflow from the combustion chamber tube 23 through an annular space 89 between the drum 24 and the combustion chamber tube 23 and then through the gap 86 and into the combustion chamber tube 23 again. The entire interior space of the combustion chamber tube 23 is considered to be the combustion chamber 22, though the flame is generally retained in the diverging flame region 65 of the combustion chamber 22. The operation of the burner assembly 76 controls the position of the flame within the chamber 22, while the combustion chamber tube 23 itself functions as a heat transfer mechanism to conduct and radiate heat to the material 30 as it advances through the annular space 89 between the drum 24 and the combustion chamber tube 23.

The annular space 89 constitutes a solid material cleansing region while, within the interior space of the combustion chamber tube 23, the heat energy is generated for the heat cleaning process. The rotation of the combustion chamber tube 23 within the drum 24 allows each longitudinal sector of the combustion chamber tube 23 to cycle through direct contact with material and then direct contact with reflow gases, as the drum 24 completes each revolution. As will become apparent, the cooperative interaction of the combustion chamber tube 23 with the drum 24, in forming the annular space 89 therebetween, and of the annular gap 86 between the tube 23 and the burner nozzle 79, constitute the basis for a first and major emission cleaning step. As will be recognized, the combustion gases are induced to reflow through the annular space 89 by a pressure reduction of the gases in the discharge chamber 78. The annular seal 72 between the drum 24 and the discharge chamber 78 already supports a certain gas deficiency within the discharge chamber 78 to cause combustion gases to be drawn from a reflow stream through the annular space 89 in a direction of arrow 91. An annular seal 92 between the material discharge housing 71 and the burner assembly 76 similarly seals off any remaining matching gap in the opening 77 about the burner assembly 76. The discharge end 58 of the drum 24 is effectively closed off or shielded from an influx of ambient air by the material discharge housing 71, the sealing effect of the material discharge housing 71 being reinforced by the discharge gate 74 and the seals 72 and 92. Thus, consistent with Bernoulli's law, high speed gases flowing from the converging nozzle 79 into the combustion chamber tube 23 generate a reduced pressure in the gap 86. The relatively low pressure with respect to the ambient draws gases from the discharge chamber 78 into the combustion chamber tube 23, generating a pressure reduction within the discharge chamber 78.

On the other hand, combustion gases exiting the combustion chamber tube 23 at the boundary section 49 are at an increased total energy level of combined potential and kinetic energy with respect to the gases within the material discharge chamber 78. The combustion gases exiting the combustion chamber tube 23 are met with a flow resistance from an impinging curtain of the falling material 30 advancing through the first heating zone 41 of the drum unit 18. A resulting pressure increase at an outflow end 94 of the combustion chamber tube 23, in combination with a low pressure region within the gap 86 at the converging intake section 63 of the tube 23, induces a significant portion of the combustion gases exiting from the combustion chamber tube 23 to be diverted through the annular space 89 to be recirculated through the combustion chamber tube 23.

It will become apparent from the foregoing that the material 30 crossing the boundary 49 and entering the second heating zone 42 no longer advances in a counterflow to the combustion gases but, instead, advances in the same direction or in a co-current direction with the reflow combustion gases in the direction of the arrow 91. The material 30 is advanced through the second heating zone 42, again, by lifting or bucket type flights 96. The bucket type flights 96 are, in accordance herewith, of a height which optimally enables the flights 96 to lift the material 30 within the available annular space 89. The bucket type flights 96 lift the material peripherally, as the drum 24 rotates, through the annular space 89 and drop the material in the form of a veil or curtain of the material 30. The combustion chamber tube 23 necessarily restricts the material 30 to movement within the annular space 89. Thus, as the material 30 is released from the flights 96, the material 30 drops onto the combustion chamber tube 23. As the material 30 drops through the re-flow or return flow 91 of combustion gases, the material 30 is heated. Actual contact of the material 30 with metal surface portions of the combustion chamber tube 23 enhances heat transfer to the material 30 within the second heating zone 42.

In the first heating zone 41, the material 30 delivered to the remediation drum unit 18 is heated, in essence, exclusively by heat transfer from the hot combustion gases moving through the veil of the material 30. The heat energy which is transferred by the heat transfer mechanism of the first heating zone 41 is therefore limited to the amount of heat carried into the first heating zone 41 by the stream of hot gases. As heat energy is transferred from the hot gases to the material, the temperature of the gases becomes decreased. It should be also realized that the material 30, when introduced into the first heating chamber of the drum 24, is likely to, and is expected to, contain a certain amount of moisture. Water would be evaporated concurrently with an initial volatilization of low boiling fractions of hydrocarbons contained in the material. Water evaporation, however, may constitute a significant heat sink for the energy brought into contact with the material 30 by the hot gases in the first heating zone 41. Thus, the hot gases, traversing the veil of the falling material within the first zone 41 of the drum 24, are of significantly reduced temperature when these hot gases exit, together with water vapor, from the feed intake housing 43. Heat transfer from the hot combustion gases is of such significance that a desired exhaust temperature of the hot gases (shown by arrow 97) as they are discharged from the feed intake housing 43 is readily obtained to lie in a range about five hundred degrees Fahrenheit (500° F.). The feed intake housing 43 consequently functions as a plenum for collecting the hot heating gases exiting the drum 24 from which the hot gases may be discharged. The temperature of the hot gases exiting from the feed intake housing 43 depends on a number of variable parameters, including the burn rate of the burner and the net flow rate of combustion gases which are not recirculated and which leave the system. The temperature of the hot gases may be controlled by a veil modification kit, for example. It is to be understood that the volume of combustion gases injected by the turbo burner assembly 76 is variable over a range which is defined by a "turn-down ratio" of the burner 76. The volume of gas flow through the first heating zone 41 is further adjusted by controlling the volume of combustion gas reflow, namely of the volume or proportion of already burned gases which are recirculated through the combustion chamber tube 23. It appears that a structure of the combustion chamber tube 23, as described, may yield a preferred reflow ratio in the order of up to one-half or 0.5. A reflow ratio of 0.5 means that about one half of the gases exiting from the combustion chamber tube outflow end 94 may be recirculated through the annular space 89 to be drawn into the tube 23 through the gap 86.

The use of the reflow of combustion gases has significant, beneficial effects on the contemplated operation of the preferred apparatus or system 10. The gaseous reflow first of all limits the gas flow and thus a gas flow velocity through the first heating zone or first heating chamber 41 of the drum 24. It may be realized that the material or soil 30 that is fed into the remediation drum unit 18 generally contains a significant amount of dust or fines. A limitation on the flow velocity of the hot gas stream through the first heating zone would also tend to limit the amount of dust that may become entrained in the gas stream to be carried off thereby to the filter 26 (see FIG. 1). A decreased volume of non-recirculated hot gases also tends to restrict the volatilization of hydrocarbon contaminants to the low boiling fractions thereof, and generally tends to pre-dry and prepare the material 30 for further treatment in the second heating zone 42 of the remediation drum unit 18. The reflow gas also functions as a buffer gas which tends to reduce the flame temperature in the combustion chamber tube 23. The low boiling fractions of hydrocarbons are found to remain in vapor form when the off gases are exhausted from the first heating zone 41 and are routed at approximately 400 to 450 degrees F. through the filter unit 26.

The heat energy of the recirculated hot gases combines with heat conducted directly through the combustion chamber tube 23 to further heat the material 30 once within the second heating zone 42 of the drum 24 to a second, higher temperature. As the material 30 enters the second heating zone 42 of the remediation drum 18, heat transfer from the now co-current flow of the heating gases through contact with the material 30 becomes therefore only one of the heating mechanisms which contribute to heating the material 30. The material 30 is further heated by radiant and by conductive heat transfer between the combustion chamber tube 23 and the material 30. Heat transfer to the material 30 in the second heating zone 42 also differs from heat transfer solely by the hot gases to the material 30 that occurred in the first heating zone 41. Both the hot gases and the wall of the combustion chamber tube 23 contribute to heating the material 30 within the annular space 89. Thus the material advancing in co-current relationship to the gases in the annular space 89 is heated on a continual basis by the hot gases, by radiant heat from the wall of the combustion chamber tube 23, and by being in direct contact with the hot gases and the hot wall of the combustion chamber tube 23. Radiant heat also may reheat the hot gas stream 91 to prolong its effectiveness as a heat storage and transfer medium within the second heating zone 42.

A risk of explosion is minimized by an exclusion of oxygen or oxidizing agents from the annular space 89. The hot gases which are recirculated through the annular space 89 have just exited from the combustion chamber 22 and are essentially depleted of free oxygen. The comparatively intense heat within the annular space 89 of the second heating zone 42 volatilizes essentially all of the heavier, long-chain hydrocarbons and any remaining lighter, short-chain hydrocarbons which may have escaped volatilization in the first heating zone 41. As the recirculated hot gases pass through the annular space 89, the heavier hydrocarbons become entrained as gases within the gaseous recirculation through the second heating zone 42. Resulting hot recirculated gases, rich with the volatilized heavier, long-chain hydrocarbons, are then drawn peripherally into the converging intake section 63 of the combustion chamber tube 23. Becoming further entrained into the stream of combustion gases exiting from the converging nozzle 79 of the turbo burner assembly 76, the hydrocarbon-rich recirculated gases mix with the combustion gases from the nozzle 79 during their flow into the flame region 65 of the combustion chamber tube 23. Any hot combustion gases continuing from the combustion chamber tube 23 into the first heating zone 41 without being recirculated are thus essentially free of heavy, long-chain hydrocarbon fractions.

Adjustments may be made to combustion air and fuel mixture ratios generated by the turbo burner assembly 76. The adjustments would account for fuel contents in the recirculated gases for essentially complete combustion, including full break-down of the volatilized hydrocarbon fractions fed into the combustion chamber tube 23 in the described manner.

Figure 4:
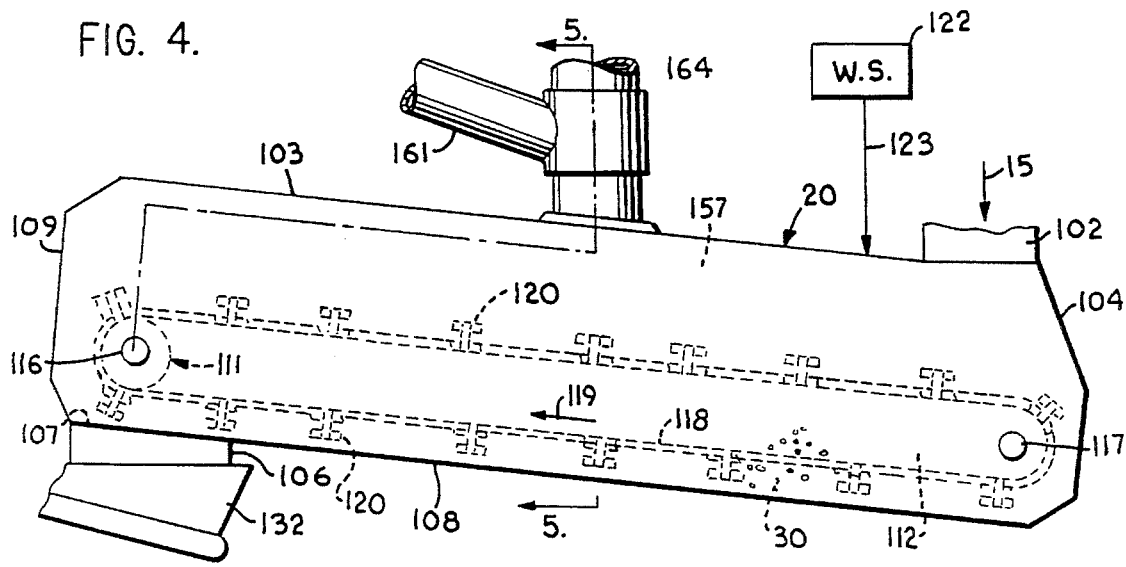
FIG. 4 is a somewhat simplified, cut away side elevation of a solid material reconstitution unit in accordance herewith.

In reference to FIGS. 1 and 4, the material 30 is discharged from the remediation drum unit 18 to be transferred, such as by a closed lift conveyor unit 101, to be fed into a drop chute or material intake chute 102 of the soil reconstitution unit 20, as shown by arrow 15. The soil reconstitution unit 20 is preferably an elongate structure of rectangular cross section, formed by a conveyor housing 103. The conveyor housing 103 is substantially closed to external access except for material flow openings. One of the openings is the intake chute 102. The intake chute 102 penetrates the conveyor housing 103 adjacent to a first end or feed end 104. A product discharge chute 106, which receives the discharged material 30 through an opening 107 in a base plate 108 of the conveyor housing 103, is disposed adjacent to a second end 109, which is also a discharge or forward end 109 opposite the feed end 104 of the conveyor housing 103.

Interiorly of the conveyor housing 103, a conveyor, designated generally by the numeral 111, is mounted in a lower material reconstitution cavity 112. The conveyor 111 has, preferably, a forward sprocket pulley and drive assembly 116 disposed adjacent to the forward end 109 and a counter sprocket pulley assembly 117 disposed adjacent to the feed end 104 of the conveyor housing 103. The forward sprocket pulley and drive assembly 116 may be coupled to a power source (which may be part of the assembly 116 as shown), which is adapted to advance in a continuous operation one or more longitudinally parallel endless loops of drive chains 118, which are stretched over pulleys of the pulley assemblies 116 and 117. It will be realized that a single endless loop of the drive chains 118, though a technical possibility, may cause transverse instability when material is advanced longitudinally. On the other hand, two identical endless loops of the drive chains or conveyor chains 118 is readily seen as providing a transversely balanced pulling mechanism. More than two equally spaced loops of the chains 118 are of course possible and may actually be preferred, as will become apparent from the further description hereof. Operating the conveyor 111 by a single driven pulley, such as by solely driving the forward sprocket pulley and drive assembly 116, may be desirable. However, it may be possible to drive both the forward sprocket pulley and drive assembly 116 and the counter sprocket pulley assembly 117, each with a portion of the power needed to advance the material 30. An operational direction of rotation of the assemblies 116 and 117 would be to cause a respective portion of each such chain 118 adjacent to the base plate 108 of the housing 103 to move in a forward direction indicated by arrow 119.

Figure 5:
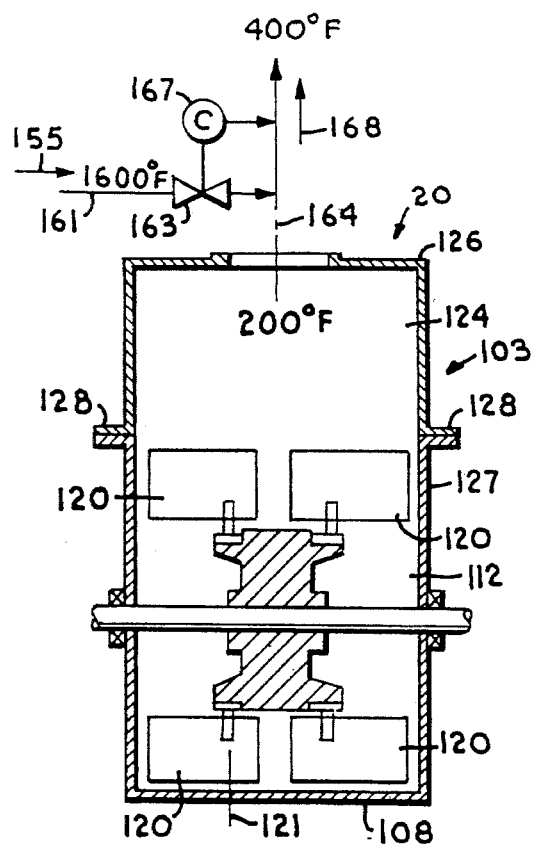
FIG. 5 is a cross-sectional view of the solid material reconstitution unit of FIG. 4.

The conveyor 111 may be a type known as a slat conveyor having transverse bars or slats extending typically the entire width of the conveying path of the conveyor 111. As will be realized, two of the endless loops of the drive chains 118 provide transverse stability in pulling the slats in the longitudinal direction of the conveyor 111. In a particular embodiment described herein, the conveyor 111 is a modified slat conveyor 111 in which typical slats have been replaced with groups of paddles 120, which are equally spaced along the chains 118 of the conveyor 111. Though two of the loops of the conveyor chains 118 are shown, it will become apparent from the following description that a plurality or more than two of the loops of chains 118 may be used for soil reconstitution units of relatively wider width than described herein. Referring to FIGS. 4 and 5, each of the paddles 120 is mounted to the respective chains 118 via a pivot link 121, the pivot link 121 being a stud which functions as an axis of rotation 121 for the respective paddle 120. The orientation of the stud or axis of rotation 121 is preferred to lie along intersecting orthogonal planes, a vertical plane in the direction of movement of the chains 118 and a second plane transverse to the direction of movement of the chains 118. The paddles 120 themselves may be substantially rectangular in shape. The paddles 120 would be mounted in a plane generally transverse to the longitudinal movement of the conveyor chains 118. However, a rotational adjustment position of the paddles 120 about the axis 121 is preferred to be at an angle of deviation with respect to such a transverse plane and toward the direction of movement of the chains 118. An orientation of the paddles 120 at an angle with respect to the direction of forward movement of the paddles 120 causes the material 30 to be "plowed" or stirred as the material 30 is moved along by the paddles 120, rather than just being advanced from the feed end 104 to the discharge end 109. The amount of rotation from a transverse plane may be one of choice and may depend on the consistency of the material 30 or the desired speed of operation of the conveyor 111. An adjustment might, therefore, be made at the beginning of a job or during normal maintenance periods of the system 10 to optimize the operation of the conveyor 111 to the satisfaction of an operator. When the paddles 120 are adjusted to an optimum angular orientation, the material 30 is urged to undergo a mixing motion in a rotational flow pattern in a transverse plane with respect to a generally longitudinal advancing movement of the material 30. The induced mixing motion in the material 30 aids a material reconstituting function which is expected to be performed by the soil reconstitution unit 20.

The use of the described chain and paddle conveyor as a preferred embodiment of the conveyor 111 holds an advantage which requires further explanation. A material mixing apparatus, which is known in the asphalt mixing art, is a pugmill. A pugmill has longitudinally disposed parallel shafts with paddle shafts extending helically pitched about each of the shafts. The use of a pugmill may be a choice for reconstituting soil. The described soil reconstitution unit 20 with the conveyor 111 as described offers a hidden advantage of having a tramp iron or oversize material release mechanism in the fact that the chains 118 can yield in a direction transverse to their longitudinal movement. Thus, though the paddles 120 would under normal conditions advance along the base plate 108 pulling along the material 30, the chains 118 will yield to permit the paddles 120 to resiliently yield to a larger rock or other odd sized piece included in the material 30 to minimize a chance of clogging the soil reconstitution operation.

The material 30 which is loaded into the soil reconstitution unit 20 through the feed chute 102 is at an elevated temperature, which may exceed under normal operation conditions of the material remediation drum unit 18, a temperature of 1000° or even 1200° F. At such elevated temperatures, all moisture becomes superheated steam. Thus, no moisture remains in the decontaminated soil material 30 when it leaves the discharge chute 73. It is incumbent to cool and re-introduce moisture into the remediated material 30 before the remediation process is completed. Water is consequently introduced into the soil reconstitution unit 20 from a water reservoir 122, which is coupled via a water line 123 to the conveyor housing 103 adjacent to the feed end 104, as shown schematically in FIG. 4.

As water is introduced into the conveyor housing 103 and contacts the hot material 30, steam is generated. The steam generation may be extensive and somewhat violent. The steam may carry off dust particles or fines contained in the remediated soil material 30. The steam is collected and retained in an upper steam chamber 124, also referred to as steam dome 124 which is enclosed by an upper housing shell 126. The upper housing shell 126 may be mounted to a lower housing shell 127 by mutually joined flanges 128, as shown in FIG. 5. A rate of flow of water through the water line 123 would preferably be adjusted to cause a certain amount of water to be retained by the material 30 after initial amounts of water have cooled the soil material to a temperature in a desired range below the boiling point of water, hence to about 200 degrees F. The mixing action by the paddles 120 on the soil material 30 is intended to mix such water residues into the bulk of the soil material 30 to reconstitute the material 30 to a useful soil consistency. The reconstituted material 30 is then discharged through the product discharge chute 106 into a receiving hopper 132 of the product delivery conveyor 21. As shown in FIG. 1, the product delivery conveyor 21 may deliver the product material 30 to a vehicle (not shown) or to a holding pile of the material 30. An operations control station 133 is schematically shown by a dashed arrow function 134 as being functionally coupled to the solid material remediation system 10. The operations control station 133 would preferably include a typical enclosed operator's shelter containing power controls and monitoring gauges including typical temperature and emissions analysis gauges. The arrow 134 represents typical industrial quality communications and power cables which are routed to the various, described pieces of apparatus of the solid material remediation system 10. Through such communications and power cables, the status of the system 10 is monitored and controls are exercised by an operator in accordance with the processes as described herein.

3. The Emission Cleaning System

A first stage of the emission cleaning subsystem 14 is within the solid material remediation drum unit 18 and is consequently shared with the solid material decontamination subsystem 12. The first stage of the emission cleaning subsystem 14 resides in the second heating zone 42 of the drum unit 18. The combustion process taking place within the described combustion chamber tube 23 ideally oxidizes substantially all, or at least a major portion of unwanted contaminants generated by heating the material 30 to the peak temperature within the second heating zone 42. It will be realized that all of the reflow gases which are drawn into the annular space 89 will recirculate through the interior of the combustion chamber tube 23, hence through the flame region 65. It is significant to note that in addition, all gases that are generated within the annular space 89 are also drawn through the low pressure gap 86 and flow through the flame region 65. Within the annular space 89, the volatizing hydrocarbons mix with the reflow gases. Further mixing takes place when the volatilized hydrocarbons and the reflow gases flow around the end of the combustion chamber tube 23 to be drawn into the gap 86. In being drawn into the stream of a combustible mixture of fuel and gases emitted at a high speed from the burner nozzle 79, the reflow gases and the volatilized hydrocarbons become mixed with the combustible gases, wherein contact of the heated hydrocarbons with oxygen may start immediate combustion. The reflow gas stream entering and mixing with the combustible air and fuel mixture from the turbo burner unit 76 is, at the point of contact, a hot mixture of fully burned gases from the previous round of combustion in the flame region 65 and the forward combustion chamber extension 67 and hydrocarbons. In fact, some lighter hydrocarbon fractions, though with low boiling points, will not become volatilized until the material 30 actually has entered the annular space 89 adjacent to the combustion chamber 22. All of the high boiling point fractions of hydrocarbons and a substantial portion of the lighter hydrocarbons consequently mix with the gas and fuel mixture injected from the burner nozzle 79 and are caused to flow through the flame region 65 of the combustion chamber tube 23. The combustion process in the flame region 65 causes substantial combustion (oxidation) of hydrocarbons into generally water and carbon dioxide, pursuant to a typical combustion process of hydrocarbon type fuels. The reflow of already burned gases will function as buffer gases to control the flame temperature and thereby reduce the risk that excess formation of nitrous oxides will occur.

Thus, the gas emission cleaning process in the combustion chamber 22 includes also the combustion of some of the lighter, more volatile fractions of hydrocarbons when these fractions are thermally extracted from the material 30 after the material 30 enters or closely approaches the annular space 89. The thermal treatment of all gases from the annular space 89 ideally also results in oxidation of substantially all high boiling point fractions of hydrocarbons, in essence all remaining hydrocarbons extracted from the material 30 passing through the annular space 89 of the combustion chamber 22. All volatilized hydrocarbons necessarily pass through the flame region 65 within the combustion chamber tube 23. These gases are mixed with hot reflow gases and with the fuel and air mixture to permit such substantial combustion. The reflow gases are further used to buffer the combustion process and thereby reduce an extremely high flame temperature. A control of, or controlled lowering of, a flame temperature is known to minimize the generation of nitrous oxides and keep any generated nitrous oxides to acceptable levels.

In addition to the removal of gaseous pollutants from the emitted remediation gases, it is further not only desirable but necessary to rid the gaseous effluence substantially of solid dust particles before the gases are discharged into the atmosphere. The gases 97 exiting from the drum unit 18 may be controlled to be at a temperature of about 500° F. To maintain the temperature in a range about 500° F. is important for a contemplated dust separation process. In reference to FIGS. 1 and 6, the gases 97 are routed from the drum unit 18 to a cyclone separator 136, which physically may be a pre-chamber of the cyclone and baghouse filter unit 26 and may lead directly into an antechamber 137 of a baghouse filter section 138 of the filter unit 26. Course dust, which may be centrifugally removable from the hot gases 97, becomes segregated in the cyclone separator 136. The pre-separation of at least a portion of the dust entrained in the exhaust gas stream lengthens operational periods between reverse flow cleaning operations at the baghouse filter section 138.

Figure 6:
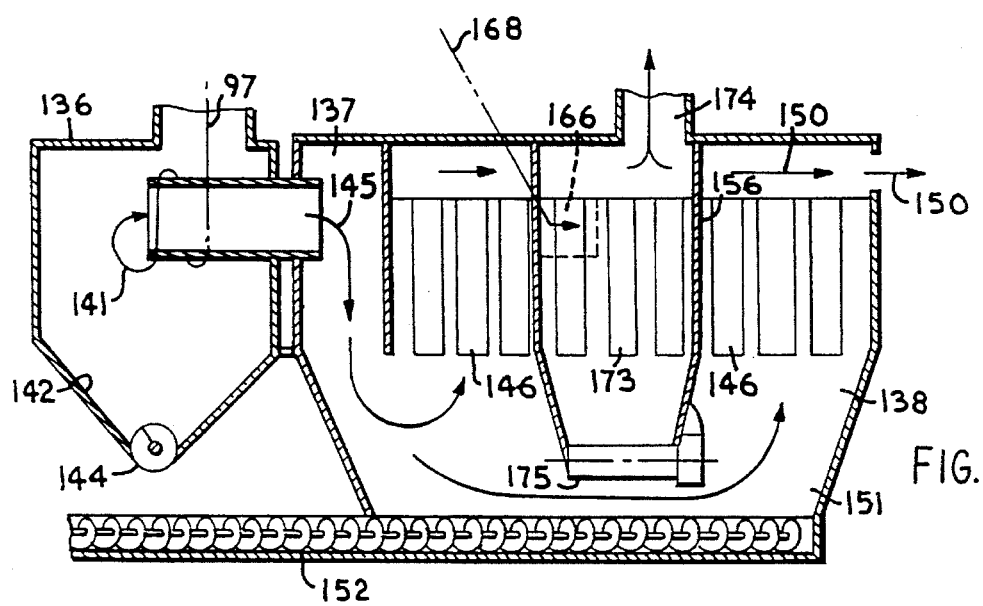
FIG. 6 is a schematically simplified cross-sectional view through a particular embodiment of a multi-chamber baghouse filter in accordance herewith.

FIG. 6 is a schematically simplified section through the filter unit 26. In the cyclone separator 136 vortex separation flow 141 of the gases separates dust to settle out to a hopper 142 from which the material may be removed through a blocking gate or a screw conveyor 144. The gases advance as pre-cleaned or pre-filtered gases 145 into the baghouse filter section 138 and pass through a battery of filter bags 146. The entrained fine dust is retained by the filter bags 146 and the gases pass as fully filtered gases 150 to a subsequent cleaning station, which is, in the particular described embodiment, the oxidizer or afterburner unit 27 as shown in FIG. 1.

Referring back to FIG. 6, maintaining the filter unit 26 operational involves care to avoid precipitation of liquids, either volatilized hydrocarbons or steam, which is generated in the first heating zone 41 of the remediation drum unit 18. The gas streams 97, 145 and 150 are all from a gaseous consistency, the same except that a different concentration of dust would normally be present in each of the streams. The filterhouse 138 uses, in the preferred example, high temperature filter bags 146 which are not affected when the gas flows through the material of the filter bags 146 at a temperature of about 500° F. It is therefore desirable to retain the temperature of the exhaust gases through the filter unit 26 at an elevated temperature to avoid precipitation of water and particularly of lower boiling fractions of hydrocarbons which may be contained in the hot gases while the gases are being cleaned of dust particles. Precipitation of particularly hydrocarbons tends to cake dust deposits and adhere the dust deposits on the filter bags 146, clogging the filter bags 146 and causing downtime. Though some cooling may occur without precipitation, the filter unit 26 is desirably compact. A desirable direct transfer from the cyclone separator 136 to the filterhouse 138 minimizes heat loss by the hot gases to the environment. In the absence of precipitation of hydrocarbons, the dust which is filtered out of the hot pre-filtered gases 145 remains free of hydrocarbons and can be returned to and combined with the remainder of the decontaminated material 30. The dust, also referred to as fines, tends to accumulate at the filter bags 146 and periodically drop into a dust hopper 151. A periodically applied gaseous reverse flow generally maintains the filter bags 146 free of clogging dust accumulations. An auger conveyor 152 or other suitable transfer mechanism transfers the separated dust or fines to a recombination process with the decontaminated material 30. FIG. 1 shows schematically a fines transfer line 29 by which the filtered fines may be routed from the filterhouse 138 to the drum 24, to be conveniently combined with the soil 30. As an alternative, fines might be mixed with water from the supply 122, forming a sludge to be combined with the material 30 in the soil reconstitution unit 20.

It is understood by those skilled in the art that certain soil contaminants cannot readily be removed by a heating and oxidation operation to detoxify all of the contaminants. When contaminants other than volatilizable hydrocarbons are present in material to be decontaminated and become part of the hot gases, intermediate liquid or chemical scrubbing process steps may need to be interleaved into the process. Since a majority of soil contaminations involve almost exclusively hydrocarbons, a hydrocarbon decontamination sequence is given as an illustrative and preferred example of the operation of the system 10.

The hot, filtered gases 150 are subsequently routed from the filterhouse 138 to the afterburner unit 27 where the gases are mixed with a combustible mixture of air and fuel and are passed through the flame of the afterburner 27 to oxidize any of the low boiling point hydrocarbons which may be retained therein. Hot effluent gases 155 are routed from the afterburner 27 to the exhaust stack unit 28 through which they are released into the atmosphere.

Referring back to the filter unit 26, the filter unit 26 differs from other filter units by including a separate steam cleaning filterhouse section 156 for removing dust from effluent gases 157, such gases in the form of steam 157, which are generated within the soil reconstitution unit 20. In reference to FIGS. 1, 5 and 6, a substantial portion of the cooling water introduced into the soil reconstitution unit 20 turns to the steam 157, as the water contacts the heated material 30 contained therein. The steam 157, which collects in the steam dome 124 of the soil reconstitution unit 20, is found to be at a temperature of about 200° F. The steam 157 is generated almost explosively and entrains a significant amount of dust or fines. On the other hand, the steam, is essentially free of hydrocarbons since it is generated by contacting uncontaminated water with the fully decontaminated material 30. The hydrocarbon-free steam 157 in the soil reconstitution unit 20 is in contrast with the hot effluent gases 97 emitted from the material remediation drum unit 18, which gases are likely to contain some concentration of volatilized low boiling point hydrocarbons. It is therefore desirable to merely filter the steam 157 generated within the soil reconstitution unit 20 to rid it of entrained dust and to then release the filtered steam 157 to the atmosphere. However, the temperature at which the steam 157 is generated, namely at the boiling point of water, is in a range of 200° F. which would cause wet, caking dust deposits to form on the filter bags 146. The steam 157 emitted from the steam dome 124 is therefore heated by mixing the steam 157 with a suitable quantity of the hot effluent gases 155. An exhaust tap duct 161 is coupled into an exhaust stack 162 of the exhaust stack unit 28 and is joined through a regulator valve 163 (see the schematic duct diagram in FIG. 5) to a steam duct 164, which couples the upper housing shell 126 to a steam intake chamber 166 of the steam cleaning filterhouse section 156. The temperature of the effluent gas 155 may be in the range of 1500 to 1700 degrees F. when mixed with the steam 157 drawn into the steam duct 164. A temperature probe and control unit 167, which is coupled into the steam duct 164 past the mixing juncture with the exhaust tap duct 161, measures the temperature of a mixed exhaust and steam effluent gas 168. A control signal, which may be electrical, fluidic, hydraulic or mechanical in its operation, causes the regulator valve 163 to admit a sufficient amount of the hot exhaust gases 155 to result in an elevated temperature of the mixed steam effluent gas 168. For example, at a temperature of 400° F. the steam content in the effluent gas 168 remains dry and superheated.

In further reference to FIG. 6, the mixed effluent gas 168 is drawn through the filter section 156, which is preferably part of the filter unit 26. It is again contemplated to maintain the temperature of the mixed effluent gas 168 within a desirable temperature range without incurring undue heat loss to the environment. Having the steam filter section 156 embedded within or directly adjacent to the filterhouse 138 minimizes heat loss from the steam to the environment while the effluent gas passes through a bank of filters 173 and into a collection or manifold chamber 174. Dust removed from the superheated steam 168 is collected in an internal dust collection and separator port 175 which collects the dust and discharges it to the dust hopper 151. It is to be noted that there may be a gaseous pressure difference between the steam passing through the steam filter section 156 and the gases 145 in the main filterhouse 138. The dust collection and separator port 175 is capable of discharging the collected dust material against such expected gaseous pressure difference.

An exhaust duct 176 leads to a fan unit 177 and from the fan unit 177 through a coupling duct 178 to the exhaust stack 162. It is the operation of the fan unit 177 which, in drawing the steam from the steam filter section 156, generates a comparatively lower pressure in the steam filter section 156 relative to that in the filterhouse 138. The fan unit 177 maintains flow in the circuit to and from the exhaust stack 162 to avoid a gaseous back pressure which may cause generated steam to block the exhaust gases from being drawn from the exhaust stack 162. As a result, the temperature regulation of the steam 157 may become stifled.

4. Overall Operation of the System

Figure 7:
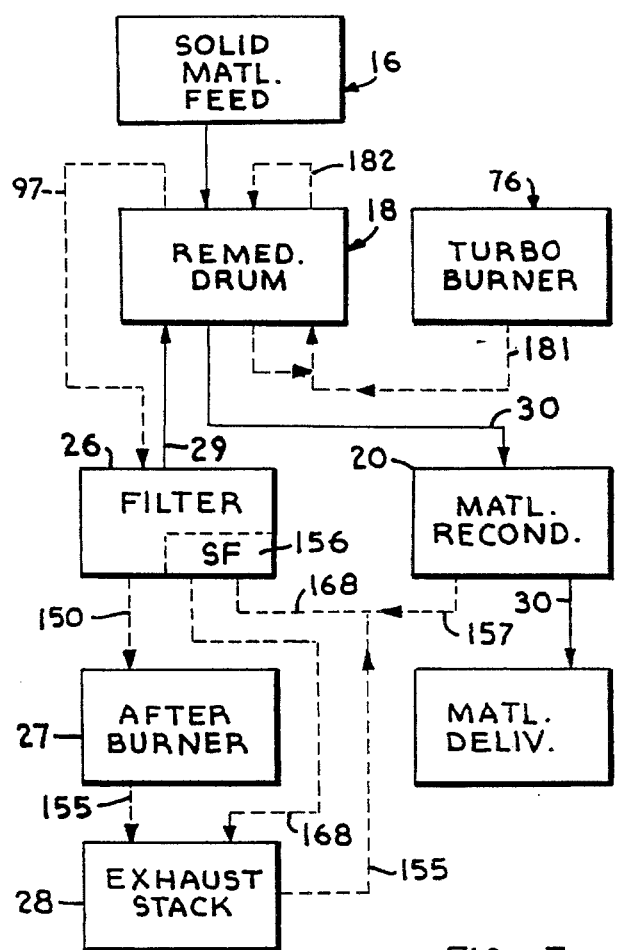
FIG. 7 is a flow diagram of the solid material remediation process and the remediation gas cleaning process showing features of the present invention.

FIG. 7 is a block diagram of the solid material remediation system 10 as described herein, and shows a summarizing overview of the described apparatus and its respective cooperative functions and flow paths of the solid material 30 (shown by solid flow lines) as well as the various gas flow patterns (shown in dotted lines in FIG. 7). The material 30 is fed from the soil preparation and feeder unit 16 (SOLID MATL FEED) to the material remediation drum unit 18 (REMED DRUM). The material 30 is then routed to the soil reconstitution unit 20 (MATL RECOND) where the material is cooled and moisture is re-introduced after substantially all of the natural moisture contained in the material 30 would have been driven off during the described heating process in the material remediation drum unit 18. After having been cooled and reconditioned to re-introduce a desired moisture content, the now decontaminated material 30 may be delivered to temporary storage or ported to a fill site, as shown by a delivery function block corresponding to the material delivery conveyor 21 (MATL DELIV), for example.

Gaseous flow originates with a combustible mixture 181 of fuel and air being injected by the turbo burner assembly 76 (TURBO BURNER) into the material remediation drum unit 18. The described internal reflow path of burned gases to feed back into the combustion chamber 22 (see FIG. 2) is identified in a diagrammatical reflow path 182. The path 182 is shown partly externally of the block 18 for illustrative purposes only. The co-current reflow path 182 of reflow gases through the material remediation drum unit 18 in contact with the material 30 results in the convective heat transfer mechanism of the described embodiment. Conductive, radiant and convective heating processes complement each other to bring the material 30 to the second temperature while the material 30 still progresses within the second heating zone of the drum unit 18. Exhaust gases 97 exiting from the material remediation drum unit 18 are directed toward the filter unit 26. Dust or fines removed from the exhaust gases while within the filter unit 26 may be routed to the drum 24, as indicated by the fines material transfer duct path 29.

The filtered exhaust gas 150 is routed to the afterburner unit 27 (AFTER BURNER) and from there, as the oxidized effluent 155, to the exhaust stack unit 28 (EXHAUST STACK). The steam 157 generated in the process of cooling the material 30 in the soil reconstitution unit 20 (MATL RECOND) is mixed with the hot effluent gas 155 to raise its temperature to about 400° F. before the mixed, superheated steam is passed through the steam filter section 156 (SF). In a preferred embodiment, the steam filter section 156 is an integral part of the filter unit 26. A particular advantage is seen in relatively higher volumes of the hot gases 97 (also described as pre-filtered gases 145 and fully filtered gases 150) continuously maintaining the walls of the steam filter section 156 at the respective temperature of such surrounding gases. As a result, substantially no heat escapes from the superheated steam 168 while the steam 168 passes through the steam filter section 156. Hence, the steam 168 may be passed through the steam filter section 156 at a lowermost non-condensing temperature.

The superheated steam 168, once separated from entrained dust, is routed to the exhaust stack unit 28 to be released to the atmosphere together with the effluent gases 155. Since the effluent gases 155 are at a relatively high temperature of 1500 to 1700 degrees F., the exhaust stack unit 28 may include a cooling operation, for example, a heat exchanger may be used to pre-heat combustion fuels or water (not shown) to implement some cooling. Also, the filtered steam 168, though superheated, is at a temperature significantly below the temperature of the effluent gases 155. Consequently, the mixing of the filtered steam 168 with the effluent gases 155 lowers the temperature of the gases before they are released to the atmosphere.

5. Modifications

As will be realized from the above detailed description, the embodiments therein are illustrative and are specific examples of apparatus and methods pursuant to the invention. Various changes and modification to the described apparatus may be made without departing from the spirit and scope of the invention.

Figure 8:
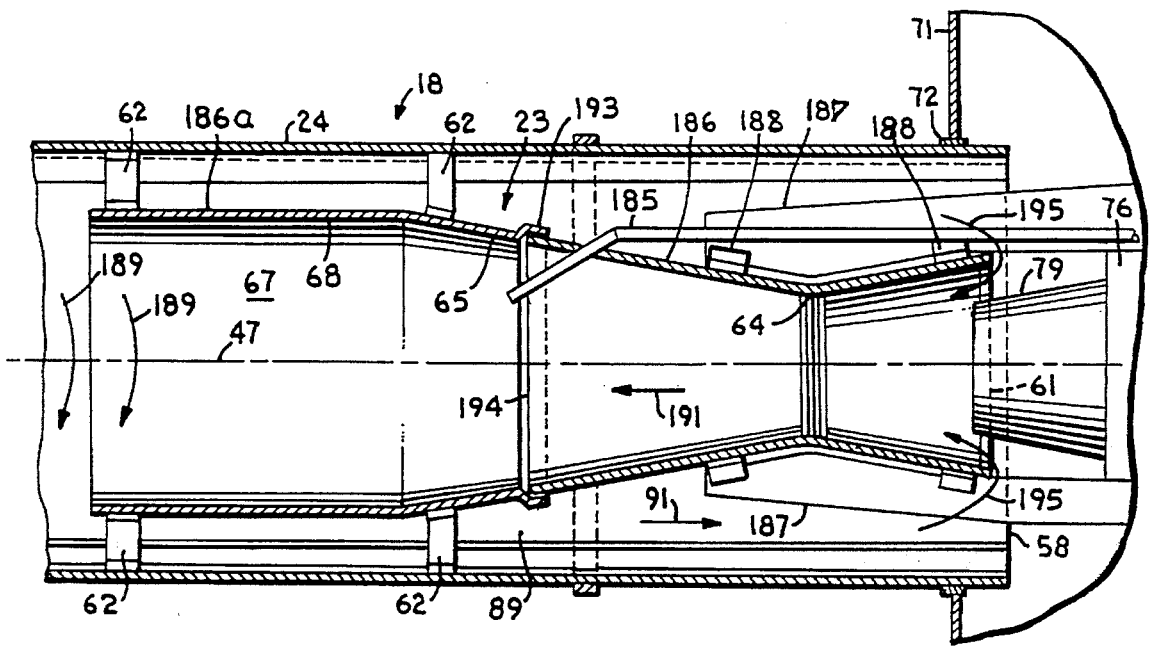
FIG. 8 is a somewhat simplified sectional view through a second heating zone of a remediation drum of an apparatus showing a split combustion chamber tube in an alternate embodiment of the present invention.

A particular modification of the combustion chamber tube 23 of the described apparatus within the scope of the invention is illustrated in FIG. 8, and relates more particularly to routing a pilot flame assembly 185 into the flame region 65 of the combustion chamber tube 23. As described with respect to the preferred embodiment (in reference to FIG. 2), the pilot flame assembly 84 is preferably inserted into the combustion chamber tube 23 from the burner assembly coaxially of the drum 24. There may, however, be design considerations pertaining to structures of particular burner assemblies, which render a concentric placement of a pilot flame assembly less than ideal. As shown in FIG. 8, the combustion chamber tube 23 may be separated into a gas injection chamber portion 186 and a combustion chamber portion 186. The gas injection chamber portion 186 is disposed adjacent to the discharge end 58 of the drum 24 and is fixedly supported with respect to the material discharge housing 71 by support plates 187. A suitable number of the support plates 187 may form part of the material discharge housing 71 and extend from the material discharge housing 71 radially arranged about the longitudinal axis 47 into the drum 24 to be attached peripherally to the gas injection chamber portion 186, such as by suitable connecting links or brackets 188. The combustion chamber portion 186a of the combustion chamber tube 23 is, as the preferred embodiment of a single piece combustion chamber tube 23 shown in FIGS. 1, 2, and 3, linked to the drum 24 by the thermal expansion links 62. Consequently, during operation of the remediation unit 18, the combustion chamber portion 186a co-rotates with the drum 24, as indicated by co-rotation arrows 189, while the gas injection chamber portion 186 remains stationary with respect to the housing 71. The pilot flame assembly 185 is routed externally of the gas injection chamber portion 186, with an entry into the diverging flame region 65 downstream of the throat or orifice section 64, considering the direction of gaseous flow 191 within the combustion chamber tube 23. To approximate a flow pattern of the gaseous flow 191 as in the single-piece combustion chamber tube 23 (FIGS. 1, 2 and 3), the combustion chamber portion 186a of the split-portion modification of the combustion chamber tube 23, shown in FIG. 8, may contain a circumferential flange 193. An adjacent end 194 of the gas injection portion 186, without impedance to the relative motion between the two tube portions 186 and 186a, is cradled by the flange 193. The discharge housing 71 is sealed against access by environmental air, the seal 72 between the stationary housing 71 and the rotatable drum 24 being an example of provisions for sealing the interior of the housing 71 from access by environmental air. Consequently, as in the above example of the preferred embodiment, a relatively low pressure is generated within the housing 71, promoting the reflow of the hot exhaust gases 91. Thus, the gaseous reflow stream 91 through the annular space 89 is drawn into the stationary gas injection portion 186 at the converging gas intake end 61 of the combustion chamber tube 23 (see flow-direction arrows 195), no different from the reflow stream 91 previously referred to in the description pertaining to the embodiment of FIG. 2.

Figure 9:
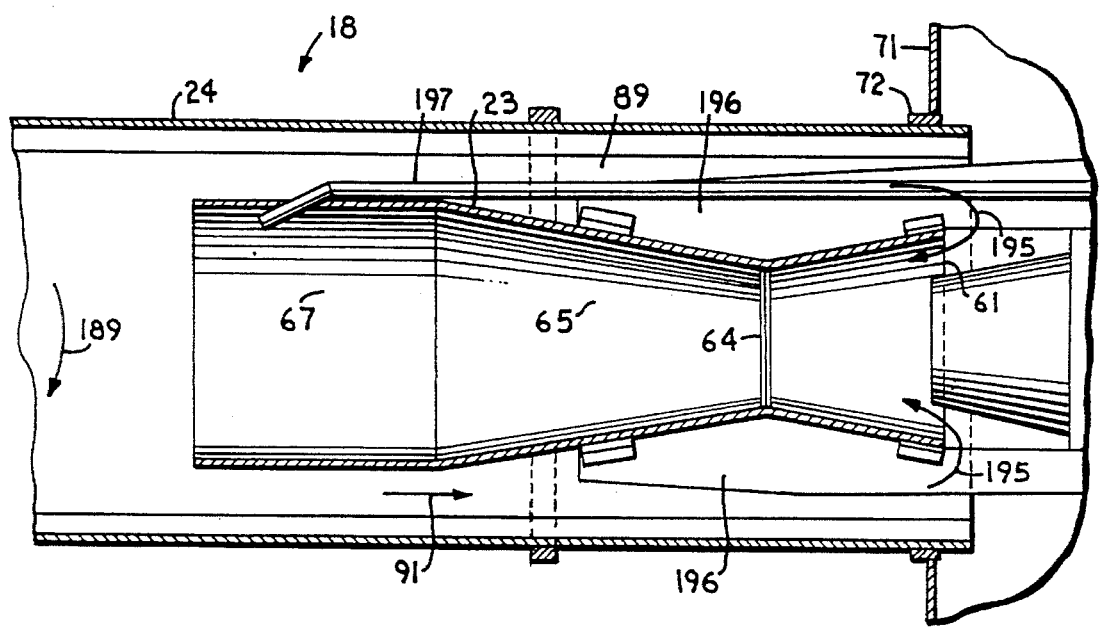
FIG. 9 is a sectional view through a second heating zone of an apparatus showing in a somewhat simplified manner a discharge end of a remediation drum with a combustion chamber tube extending in a cantilevered manner into the remediation drum.

FIG. 9 shows a further modification of the remediation unit 18, according to which the combustion chamber tube 23 is entirely supported in a cantilevered manner, supported by radially and longitudinally extending support plates 196. No part of the combustion chamber tube 23 is supported by the drum 24, such that the drum 24 may rotate with respect to the combustion chamber tube 23, as shown by the single arrow 189. A pilot flame assembly 197 may be routed externally of the combustion chamber tube 23 through the annular space 89 between the combustion chamber tube 23 and the drum 24 and may penetrate into the combustion chamber 22 at any convenient or desired point along the longitudinal extent of the combustion chamber tube 23. FIG. 9 shows, as an example, an entry point of the pilot flame assembly 197 at the forward combustion chamber extension 67 of the combustion chamber tube 23. The latter cantilever structure of the combustion chamber tube 23 may be desirable in apparatus wherein a length of the combustion chamber tube 23 is not excessive, such as in comparatively small apparatus structures.

Thus, within the scope of the inventions, various modifications may be made to the described apparatus, all of which represent embodiments within the scope of the invention. Furthermore, features disclosed as preferred apparatus in accordance with the present invention, though found to be of particular advantage to soil remediation, are seen to have broader application. One application relates, for example, to the production of asphalt products for road construction, wherein at least a portion of the aggregate material consists of recycled asphaltic material. It is advantageous to heat recycled asphaltic materials away from a hot gas stream, such as by contact with a superheated virgin aggregate material. In contrast, heating material first in a direct counterflow gas stream and then to a higher temperature in a reflow gas stream, but also substantially through contact with a combustion chamber tube, is realized in accordance herewith to be advantageous in spite of established prior practice. An advantageous distinction over prior art apparatus and processes may be seen, for example, when it is realized that the gases coming into contact with the material 30 in the annular space 89 are substantially oxygen-depleted, and all gases from the second heating zone 42, either passing through the annular space 89 between the drum 24 and the combustion chamber tube 23, or generated therein by volatilization, pass subsequently directly through the combustion chamber 22 itself.

Various other changes and modifications may be possible without departing from the scope of the invention.

What is claimed is:

1. A method of remediating a material having short-chain and long-chain hydrocarbon fractions contaminating the material, comprising:

placing a material contaminated with short-chain and long-chain hydrocarbon fractions in an intake end of a remediation drum having a discharge end opposite to the intake end of the drum, the drum having a first heating zone extending within the drum from the intake end and a second heating zone continuing within the drum from the first heating zone to the discharge end of the drum;

generating a stream of heated gases in a flame region of a combustion chamber tube extending concentrically within the drum and over the length of the second heating zone, the combustion chamber tube having an outflow end disposed adjacent to the first heating zone and a gas intake end disposed adjacent to the discharge end of the drum;

diverting a portion of the stream of heated gases from the outflow end of the combustion chamber tube through an annular space extending the length of the second heating zone of the drum between the drum and the combustion chamber tube toward the discharge end of the drum and into the gas intake end of the combustion chamber tube;

advancing the material through the remediation drum in a direction from the intake end of the drum toward the discharge end of the drum while repeatedly lifting and dropping the material within the drum;

exposing the material in the first heating zone to the stream of heated gases flowing through the drum in a direction counterflow to that of the material advancing through the drum and heating the material in the first heating zone to a first temperature sufficient to dry the material and to volatilize the short chain hydrocarbon fractions contaminating the material; and directing the material advancing through the drum to advance through the annular space of the second heating zone in a co-current flow with the portion of the stream of heated gases diverted from the outflow end of the combustion chamber tube, and heating the material advancing through the annular space within the second heating zone to a second temperature sufficient to volatilize the long-chain hydrocarbons fractions contaminating the material such that the long-chain hydrocarbons fractions so volatilized flow with the portion of the stream of heated gases diverted from the outflow end of the combustion chamber tube into the gas intake end of the combustion chamber tube and through the flame region thereof.

2. A method of remediating a material, comprising:

placing a material contaminated with short-chain and long-chain hydrocarbon fractions in a rotating drum having adjacent first and second heating zones therein wherein the first heating zone is adjacent to a material intake end of the drum and the second heating zone is adjacent to a material discharge end of the drum;

advancing the material from the material intake end through the first heating zone followed by advancing the material to the material discharge end of the drum through an annular space between the drum and a combustion chamber tube disposed concentrically and coextensively within the drum and within the second heating zone such that the annular space extends to the material discharge end of the drum, the combustion chamber tube having a gas intake end adjacent to the material discharge end of the drum;

directing a combustible mixture of gases from the material discharge end in and through the combustion chamber tube such that the combustible mixture of gases is ignited and to thereby generate combustion gases, the combustible mixture of gases and the combustion gases flowing toward, through the first heating zone in a direction counterflow to the flow of the material therethrough to volatilize the short-chain hydrocarbon fractions contaminating the material, and then to the materials intake end of the drum; and diverting a portion of the combustible mixture of gases and the combustion gases through the annular space between the drum and the combustion chamber tube toward the material discharge end of the drum and through the gas intake end into the combustion chamber tube to volatilize the long-chain hydrocarbon fractions contaminating the material.

3. The method according to claim 2, wherein the diverting step comprises a converging burner nozzle and a converging intake section disposed at the gas intake end of the combustion chamber tube such that an annular gap is formed therebetween, and preventing ambient air from entering the annular gap to thereby provide means for generating the low pressure in the discharge end of the drum relative to the pressure in the annular Space adjacent to the first heating zone.

4. The method according to claim 3, wherein the diverting step further comprises the step of adjusting the portion of the combustible mixture of gases and the combustion gases by adjusting the width of the annular gap.

5. The method according to claim 2, further comprising the steps of:

cooling and adding water to the material after being discharged from the drum.

6. The method according to claim 5, wherein the steps of cooling and adding water to the discharged material include:

conveying the discharged material along an elongate conveyor disposed in a housing containing steam in a steam chamber which is receiving injected water at a measured rate, the conveyor arranged to receive the discharged material.

7. The method according to claim 6, including the steps of:

exhausting the combustible mixture of gases and the combustion gases from the intake end of the drum;

filtering the the combustible mixture of gases and the combustion gases exhausted from the intake end of the drum with a filterhouse; and filtering dust from steam generated in the steam chamber by directing the steam through a segregated compartment of the filterhouse.

8. A method of remediating a material, comprising the steps of:

advancing a material contaminated with short-chain and long-chain hydrocarbon fractions from a material intake end toward a material discharge end of a rotating drum, the drum having a first heating zone therein extending inwardly from the material intake end of the drum and a second heating zone therein continuing from the first heating zone to the material discharge end of the drum;

introducing a combustible mixture from the discharge end of the drum into a combustion chamber of a combustion chamber tube disposed concentrically within the drum and extending into the drum from the material discharge end of the drum such that an annular space, which opens into the combustion chamber at the discharge end of the drum and is substantially coextensive with the second heating zone, is formed between the drum and the combustion chamber tube such that the material being advanced through the drum passes through the annular space;

igniting and sustaining combustion of the combustible mixture within the combustion chamber to generate a stream of combustion gases flowing through the combustion chamber toward the material intake end of the drum and in counterflow relation to the material being advanced through the drum;

diverting a portion of the generated combustion gases into a reflow path through the annular space in co-current relation with the material being advanced therethrough and into the combustion chamber at the discharge end of the drum to volatilize the long-chain hydrocarbon fractions contaminating the material; and directing the remaining portion of the combustion gas through the first heating zone to volatilize the short-chain hydrocarbon fractions contaminating the material and discharging the remaining portion of the combustion gases at the material intake end of the drum.

9. A method of remediating a material having short-chain and long-chain hydrocarbon fractions contaminating the material, comprising:

placing a material contaminated with short-chain and long-chain hydrocarbon fractions in an intake end of a remediation drum having a discharge end opposite to the intake end of the drum, the drum having a first heating zone extending within the drum from the intake end and a second heating zone continuing within the drum from the first heating zone to the discharge end of the drum;

providing and directing a stream of combustible gas into a gas intake end of a combustion chamber tube for generating a stream of heated gases in a flame region of the combustion chamber tube extending concentrically within the drum and over the length of the second heating zone, the combustion chamber tube having an outflow end disposed adjacent to the first heating zone and a gas intake end disposed adjacent to the discharge end of the drum;

diverting a portion of the stream of heated gases from the outflow end of the combustion chamber tube through an annular space extending the length of the second heating zone of the drum between the drum and the combustion chamber tube toward the discharge end of the drum and into the gas intake end of the combustion chamber tube, wherein said portion of the stream of heated gases is diverted by providing a velocity stream of combustible gas sufficient to generate a reduced pressure at the gas intake end with respect to gas pressure at the outflow end and by sealing the gas intake end from access by environmental air;

advancing the material through the remediation drum in a direction from the intake end of the drum toward the discharge end of the drum while repeatedly lifting and dropping the material within the drum;

exposing the material in the first heating zone to the stream of heated gases flowing through the drum in a direction counterflow to that of the material advancing through the drum and heating the material in the first heating zone to a first temperature sufficient to dry the material and to volatilize the short chain hydrocarbon fractions contaminating the material; and directing the material advancing through the drum to advance through the annular space of the second heating zone in a co-current flow with the portion of the stream of heated gases diverted from the outflow end of the combustion chamber tube, and heating the material advancing through the annular space within the second heating zone to a second temperature sufficient to volatilize the long-chain hydrocarbons fractions contaminating the material such that the long-chain hydrocarbons fractions so volatilized flow with the portion of the stream of heated gases diverted from the outflow end of the combustion chamber tube into the gas intake end of the combustion chamber tube and through the flame region thereof.

10. A method of remediating a material, comprising:

placing a material contaminated with short-chain and long-chain hydrocarbon fractions in a rotating drum having adjacent first and second heating zones therein wherein the first heating zone is adjacent to a material intake end of the drum and the second heating zone is adjacent to a material discharge end of the drum;

advancing the material from the material intake end through the first heating zone followed by advancing the material to the material discharge end of the drum through an annular space between the drum and a combustion chamber tube disposed concentrically and coextensively within the drum and within the second heating zone such that the annular space extends to the material discharge end of the drum, the combustion chamber tube having a gas intake end adjacent to the material discharge end of the drum;

directing a combustible mixture of gases from the material discharge end in and through the combustion chamber tube such that the combustible mixture of gases is ignited and to thereby generate combustion gases, the combustible mixture of gases and the combustion gases flowing toward and through the first heating zone in a direction counterflow to the flow of the material therethrough to volatilize the short-chain hydrocarbon fractions contaminating the material and then to the material intake end of the drum; and diverting a portion of the combustible mixture of gases and the combustion gases through the annular space between the drum and the combustion chamber tube toward the material discharge end of the drum to volatilize the long-chain hydrocarbon fractions contaminating the material and through the gas intake end into the combustion chamber tube by generating a low pressure at the discharge end of the drum relative to pressure in the annular space adjacent to the first heating zone.

* * * * *

UNITED STATES PATENT AND TRADEMARK OFFICE
CERTIFICATE OF CORRECTION

PATENT NO. : 5,455,005

DATED : October 3, 1995

INVENTOR(S) : Clawson et al.

It is certified that error appears in the above-identified patent and that said Letters Patent is hereby corrected as shown below:     On title page, item [56]

In the "References Cited" section, delete "4,427,293  5/1984  Campbell  405/126"; insert after "4,925,389  5/1990  Decicco et al  432/106" --4,927,293  5/1990  Campbell  405/126-- .

In Column 6, line 54:  delete "5";

In Column 8, lines 23 and 24:  delete ",also referred to herein as discharge chute 73" ;

In Column 8, line 24:  after the second "73", insert --also referred to herein as discharge chute 73,-- ;

In Column 15, line 24:  delete "System" and substitute therefor --Subsystem-- ;

Column 16, line 37, delete "Course" and insert therefor --Coarse--

In Column 17, line 50:  after "such" insert --as-- ;

Col. 17, line 58, delete "steam," substitute --steam 157--

In Column 20, line 15:  delete the first "186" and substitute therefor --186a--;

In Column 20, line 55:  delete "converging" ;

In Claim 2, Column 22, line 51:  delete "materials" and insert therefor --material-- ;

In Claim 3, Column 22, line 60:  after "comprises", insert --providing-- ;

In Claim 3, Column 22, line 66:  delete "Space" and substitute therefor --space-- ;

UNITED STATES PATENT AND TRADEMARK OFFICE
CERTIFICATE OF CORRECTION

PATENT NO.    :  5,455,005

DATED         :  October 3, 1995

INVENTOR(S)  :  Clawson et al.

It is certified that error appears in the above-identified patent and that said Letters Patent is hereby corrected as shown below:

In Claim 8, Column 23, line 61:   delete "gas" and insert therefor
    --gases-- ;

In Claim 9, Column 24, line 27:   after "velocity", insert --for the-- ;

Signed and Sealed this

Twenty-third Day of April, 1996

Attest:

BRUCE LEHMAN

Attesting Officer       Commissioner of Patents and Trademarks